United States Patent [19]
Smith et al.

[11] Patent Number: 6,060,448
[45] Date of Patent: May 9, 2000

[54] CASEIN FRAGMENTS HAVING GROWTH PROMOTING ACTIVITY

[75] Inventors: John Arthur Smith, Liverpool; Mark Charles Wilkinson, Wirral; Qing-Ming Liu, Liverpool, all of United Kingdom

[73] Assignee: Pepsyn Limited, Liverpool, United Kingdom

[21] Appl. No.: 09/066,408

[22] PCT Filed: Oct. 31, 1996

[86] PCT No.: PCT/GB96/02658

§ 371 Date: Jul. 13, 1998

§ 102(e) Date: Jul. 13, 1998

[87] PCT Pub. No.: WO97/16460

PCT Pub. Date: May 9, 1997

[30] Foreign Application Priority Data

Oct. 31, 1995 [GB] United Kingdom .................... 9522302

[51] Int. Cl.⁷ .................................................. A61K 38/00
[52] U.S. Cl. ................................. 514/12; 514/13; 514/14; 514/15
[58] Field of Search ................................ 514/12, 13, 14, 514/15

[56] References Cited

FOREIGN PATENT DOCUMENTS

| 0457 565 A2 | 5/1991 | European Pat. Off. ......... A61K 7/06 |
| 03 255 095 | 3/1990 | Japan . |
| 06 211 689 | 1/1993 | Japan .............................. A61K 37/18 |

OTHER PUBLICATIONS

*Biochem. Soc. Trans.*, vol. 24, No. 3, 1996, p. 342S, Liu, Q.: "A growth factor activity in bovine milk" 658th Meeting Liverpool—Held at the University of Liverpool Apr. 16–19, 1996.

Kizawa et al., *Chem Abstracts*, 121:292792.

*Primary Examiner*—Avis M. Davenport
*Attorney, Agent, or Firm*—Townsend & Townsend & Crew

[57] ABSTRACT

Amino acid sequences substantially identical to the C-terminal end of an α-S2 casein precursor one shown to act as growth promoters.

Disclosed are sequences from Bovine α-S2 casein including the 9 C-terminal amino acids.

LysValIlEProTyrValArgTyrLeu (SEQ ID NO:1)

Also disclosed are foodstuffs and medicaments comprising the peptides of the invention and a method of producing same.

28 Claims, 4 Drawing Sheets

Table 1. Partial purification of growth promoting activity from 5.1 litres of bovine semi-skimmed milk

| | Volume (ml) | Total protein (mg) | Total act. (units) | Spec.act. (units/mg) | Recovery (%) per step | Recovery (%) in total | Fold of purification per step | Fold of purification in total |
|---|---|---|---|---|---|---|---|---|
| Crude milk | 5100 | 173,400 | 236,612 | 1.36 | 100 | 100 | 1 | 1 |
| Acid extraction | 3650 | 12,008 | 217,884 | 18.14 | 92.1 | 92.1 | 13.34 | 13.34 |
| (NH₄)₂SO₄ salt out | 1605 | 4,397 | 88,789 | 20.19 | 40.1 | 37.5 | 1.11 | 14.85 |
| CM-sepharose chromatography | 165 | 27.15 | 38,975 | 1,435.5 | 46.1 | 16.5 | 74.49 | 1,055.51 |
| Hydrophobic interaction chromatography | 73.5 | 2.31 | 28,998 | 12,553.2 | 74.4 | 12.26 | 8.75 | 9,230.29 |
| Reversed phase HPLC (C4 column) | 11.05 | 0.021 | 8,010 | 381,428.6 | 27.6 | 3.4 | 30.38 | 280,462.2 |
| Reversed phase HPLC (C18 column) | 0.48 | 0.015 | 702 | 46,800 | 8.8 | 0.3 | — | 34,411.76 |

FIG. 6

```
                        SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:1:

Lys Val Ile Pro Tyr Val Arg Tyr Leu
1               5

(2) INFORMATION FOR SEQ ID NO:2:

(i) SEQUENCE CHARACTERISTICS:
          (A) LENGTH: 10 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:2:

Thr Lys Val Ile Pro Tyr Val Arg Tyr Leu
1               5                   10

(2) INFORMATION FOR SEQ ID NO:3:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:3:

Lys Thr Lys Val Ile Pro Tyr Val Arg Tyr Leu
1               5                   10

(2) INFORMATION FOR SEQ ID NO:4:

(i) SEQUENCE CHARACTERISTICS:
          (A) LENGTH: 19 amino acids
          (B) TYPE: amino acid
          (C) STRANDEDNESS:
          (D) TOPOLOGY: linear
```

(ii) MOLECULE TYPE: peptide (xi) SEQUENCE DESCRIPTION: SEQ ID NO:4:

Ala Met Lys Pro Trp Ile Gln Pro Lys Thr Lys Val Ile Pro Tyr Val
1               5                   10                  15

Arg Tyr Leu (2) INFORMATION FOR SEQ ID NO:5:

(i) SEQUENCE CHARACTERISTICS:
        (A) LENGTH: 31 amino acids
        (B) TYPE: amino acid
        (C) STRANDEDNESS:
        (D) TOPOLOGY: linear     (ii) MOLECULE TYPE: peptide     (xi) SEQUENCE DESCRIPTION: SEQ ID NO:5:

Pro Gln Tyr Leu Lys Thr Val Tyr Gln His Gln Lys Ala Met Lys Pro
1               5                   10                  15

Trp Ile Gln Pro Lys Thr Lys Val Ile Pro Tyr Val Arg Tyr Leu
            20                  25                  30

(2) INFORMATION FOR SEQ ID NO:6:

(i) SEQUENCE CHARACTERISTICS:
        (A) LENGTH: 222 amino acids
        (B) TYPE: amino acid
        (C) STRANDEDNESS:
        (D) TOPOLOGY: linear     (ii) MOLECULE TYPE: protein     (ix) FEATURE:
        (A) NAME/KEY: Protein
        (B) LOCATION: 1..222
        (D) OTHER INFORMATION: /note= "bovine alpha-S2 casein
            precursor"

(xi) SEQUENCE DESCRIPTION: SEQ ID NO:6:

Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
            35                  40                  45

Asn Leu Cys Ser Thr Phe Cys Lys Glu Val Val Arg Asn Ala Asn Glu
        50                  55                  60

Glu Glu Tyr Ser Ile Gly Ser Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
            115                 120                 125

Arg Asn Ala Val Pro Ile Thr Pro Thr Leu Asn Arg Glu Gln Leu Ser
        130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Glu Lys Asn Arg Leu

```
                    165                 170                 175
Asn Phe Leu Lys Lys Ile Ser Gln Arg Tyr Gln Lys Phe Ala Leu Pro
                180                 185                 190

Gln Tyr Leu Lys Thr Val Tyr Gln His Gln Lys Ala Met Lys Pro Trp
            195                 200                 205

Ile Gln Pro Lys Thr Lys Val Ile Pro Tyr Val Arg Tyr Leu
        210                 215                 220

(2) INFORMATION FOR SEQ ID NO:7:

(i) SEQUENCE CHARACTERISTICS:
        (A) LENGTH: 223 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..223
        (D) OTHER INFORMATION: /note= "goat alpha-S2 casein
            precursor allele A"

(xi) SEQUENCE DESCRIPTION: SEQ ID NO:7:

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asn
    50                  55                  60

Glu Glu Glu Tyr Ser Ile Arg Ser Ser Glu Glu Ser Ala Glu Val
65                  70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
    130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
    210                 215                 220

(2) INFORMATION FOR SEQ ID NO:8:

(i) SEQUENCE CHARACTERISTICS:
        (A) LENGTH: 223 amino acids
        (B) TYPE: amino acid
        (C) STRANDEDNESS:
```

-continued

```
        (D) TOPOLOGY: linear (ii) MOLECULE TYPE: protein (ix) FEATURE:
        (A) NAME/KEY: Protein
        (B) LOCATION: 1..223
        (D) OTHER INFORMATION: /note= "goat alpha-S2 casein
            precursor allele B"

(xi) SEQUENCE DESCRIPTION: SEQ ID NO:8:

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30

Gln Glu Ile Tyr Lys Gln Lys Asn Met Ala Ile His Pro Arg Lys
        35                  40                  45

Glu Lys Leu Cys Thr Thr Ser Cys Glu Glu Val Val Arg Asn Ala Asn
50                  55                  60

Glu Glu Glu Tyr Ser Ile Arg Ser Ser Ser Glu Glu Ser Ala Lys Val
65                  70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
                100                 105                 110

Gln Tyr Pro Tyr Gln Gly Pro Ile Val Leu Asn Pro Trp Asp Gln Val
            115                 120                 125

Lys Arg Asn Ala Gly Pro Phe Thr Pro Thr Val Asn Arg Glu Gln Leu
130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
                180                 185                 190

Pro Gln Tyr Leu Lys Thr Val Asp Gln His Gln Lys Ala Met Lys Pro
            195                 200                 205

Trp Thr Gln Pro Lys Thr Asn Ala Ile Pro Tyr Val Arg Tyr Leu
210                 215                 220

(2) INFORMATION FOR SEQ ID NO:9:

(i) SEQUENCE CHARACTERISTICS:
        (A) LENGTH: 223 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..223
        (D) OTHER INFORMATION: /note= "goat alpha-S2 casein
            precursor allele C"

(xi) SEQUENCE DESCRIPTION: SEQ ID NO:9:

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Phe
            20                  25                  30
```

```
Gln Glu Ile Tyr Lys Gln Glu Lys Asn Met Ala Ile His Pro Arg Lys
         35                  40                  45

Glu Lys Leu Cys Thr Thr Ser Cys Glu Glu Val Val Arg Asn Ala Asn
 50                      55                  60

Glu Glu Glu Tyr Ser Ile Arg Ser Ser Ser Glu Ser Ala Glu Val
65                   70                  75                  80

Ala Pro Glu Glu Ile Lys Ile Thr Val Asp Asp Lys His Tyr Gln Lys
                 85                  90                  95

Ala Leu Asn Glu Ile Asn Gln Phe Tyr Gln Lys Phe Pro Gln Tyr Leu
                100                 105                 110

Gln Tyr Pro Tyr Gln Gly Pro Ile Val Leu Asn Pro Trp Asp Gln Val
            115                 120                 125

Lys Arg Asn Ala Gly Pro Phe Thr Pro Thr Val Asn Arg Glu Gln Leu
130                     135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Lys Asn Arg
                165                 170                 175

Leu Asn Phe Leu Lys Ile Ile Ser Gln Tyr Tyr Gln Lys Phe Ala Trp
                180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
        210                 215                 220

(2) INFORMATION FOR SEQ ID NO:10:

(i) SEQUENCE CHARACTERISTICS:
        (A) LENGTH: 179 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..179
        (D) OTHER INFORMATION: /note= "rabbit alpha-S2 casein form
            b precursor"

(xi) SEQUENCE DESCRIPTION: SEQ ID NO:10:

Met Lys Phe Phe Ile Phe Thr Cys Leu Leu Ala Val Ala Leu Ala Lys
1               5                   10                  15

Pro Lys Ile Glu Gln Ser Ser Ser Glu Glu Thr Ile Ala Val Ser Gln
            20                  25                  30

Glu Val Ser Pro Asn Leu Glu Asn Ile Cys Ser Thr Ala Cys Glu Glu
         35                  40                  45

Pro Ile Lys Asn Ile Asn Glu Val Glu Tyr Val Glu Val Pro Thr Glu
     50                  55                  60

Ile Lys Asp Gln Glu Phe Tyr Gln Lys Val Asn Leu Leu Gln Tyr Leu
65                  70                  75                  80

Gln Ala Leu Tyr Gln Tyr Pro Thr Val Met Asp Pro Trp Thr Arg Ala
                85                  90                  95

Glu Thr Lys Ala Ile Pro Phe Ile Arg Thr Met Gln Tyr Lys Gln Glu
             100                 105                 110

Lys Asp Ala Thr Lys His Thr Ser Gln Lys Thr Glu Leu Thr Glu Glu
             115                 120                 125
```

Glu Lys Ala Phe Leu Lys Tyr Leu Asp Glu Met Lys Gln Tyr Tyr Gln
    130                 135                 140

Lys Phe Val Phe Pro Gln Tyr Leu Lys Asn Ala His His Phe Gln Lys
145                 150                 155                 160

Thr Met Asn Pro Trp Asn His Val Lys Thr Ile Ile Tyr Gln Ser Val
                165                 170                 175

Pro Thr Leu (2) INFORMATION FOR SEQ ID NO:11:

(i) SEQUENCE CHARACTERISTICS:
        (A) LENGTH: 223 amino acids
        (B) TYPE: amino acid
        (C) STRANDEDNESS:
        (D) TOPOLOGY: linear     (ii) MOLECULE TYPE: protein     (ix) FEATURE:
        (A) NAME/KEY: Protein
        (B) LOCATION: 1..223
        (D) OTHER INFORMATION: /note= "sheep alpha-S2 casein
            precursor"

(xi) SEQUENCE DESCRIPTION: SEQ ID NO:11:

Met Lys Phe Phe Ile Phe Thr Cys Leu Leu Ala Val Ala Leu Ala Lys
1               5                   10                  15

His Lys Met Glu His Val Ser Ser Ser Glu Glu Pro Ile Asn Ile Ser
                20                  25                  30

Gln Glu Ile Tyr Lys Gln Glu Lys Asn Met Ala Ile His Pro Arg Lys
            35                  40                  45

Glu Lys Leu Cys Thr Thr Ser Cys Glu Glu Val Val Arg Asn Ala Asp
50                  55                  60

Glu Glu Glu Tyr Ser Ile Arg Ser Ser Ser Glu Glu Ser Ala Glu Val
65                  70                  75                  80

Ala Pro Glu Glu Val Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
                100                 105                 110

Gln Tyr Leu Tyr Gln Gly Pro Ile Val Leu Asn Pro Trp Asp Gln Val
            115                 120                 125

Lys Arg Asn Ala Gly Pro Phe Thr Pro Thr Val Asn Arg Glu Gln Leu
130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
                180                 185                 190

Pro Gln Tyr Leu Lys Thr Val Asp Gln His Gln Lys Ala Met Lys Pro
            195                 200                 205

Trp Thr Gln Pro Lys Thr Asn Ala Ile Pro Tyr Val Arg Tyr Leu
210                 215                 220

(2) INFORMATION FOR SEQ ID NO:12:

(i) SEQUENCE CHARACTERISTICS:
        (A) LENGTH: 235 amino acids
        (B) TYPE: amino acid
        (C) STRANDEDNESS:

-continued

```
        (D) TOPOLOGY: linear (ii) MOLECULE TYPE: protein (ix) FEATURE:
        (A) NAME/KEY: Protein
        (B) LOCATION: 1..235
        (D) OTHER INFORMATION: /note= "pig alpha-S2 casein
            precursor"

(xi) SEQUENCE DESCRIPTION: SEQ ID NO:12:

Met Lys Phe Phe Ile Phe Thr Cys Leu Leu Ala Val Ala Phe Ala Lys
1               5                   10                  15

His Glu Met Glu His Val Ser Ser Ser Glu Glu Ser Ile Asn Ile Ser
                20                  25                  30

Gln Glu Lys Tyr Lys Gln Glu Lys Asn Val Ile Asn His Pro Ser Lys
            35                  40                  45

Glu Asp Ile Cys Ala Thr Ser Cys Glu Glu Ala Val Arg Asn Ile Lys
        50                  55                  60

Glu Val Gly Tyr Ala Ser Ser Ser Ser Glu Glu Ser Val Asp Ile
65                  70                  75                  80

Pro Ala Glu Asn Val Lys Val Thr Val Glu Asp Lys His Tyr Leu Lys
                85                  90                  95

Gln Leu Glu Lys Ile Ser Gln Phe Tyr Gln Lys Phe Pro Gln Tyr Leu
            100                 105                 110

Gln Ala Leu Tyr Gln Ala Gln Ile Val Met Asn Pro Trp Asp Gln Thr
        115                 120                 125

Lys Thr Ser Ala Tyr Pro Phe Ile Pro Thr Val Ile Gln Ser Gly Glu
    130                 135                 140

Glu Leu Ser Thr Ser Glu Glu Pro Val Ser Ser Ser Gln Glu Glu Asn
145                 150                 155                 160

Thr Lys Thr Val Asp Met Glu Ser Met Glu Glu Phe Thr Lys Lys Thr
                165                 170                 175

Glu Leu Thr Glu Glu Glu Lys Asn Arg Ile Lys Phe Leu Asn Lys Ile
            180                 185                 190

Lys Gln Tyr Tyr Gln Lys Phe Thr Trp Pro Gln Tyr Ile Lys Thr Val
        195                 200                 205

His Gln Lys Gln Lys Ala Met Lys Pro Trp Asn His Ile Lys Thr Asn
    210                 215                 220

Ser Tyr Gln Ile Ile Pro Asn Leu Arg Tyr Phe
225                 230                 235
```

CASEIN FRAGMENTS HAVING GROWTH PROMOTING ACTIVITY

The present invention relates to growth promoters.

It has long been known that milk contains growth promoting activity for cells that is additional to its nutritional content. Thus, Epidermal Growth Factor (EGF) has been identified in human (Shing and Klagsbrun, 1984, Petrides, 1985), rat (Raaberg et al, 1990) swine (Tan et al 1990) and goat (Brown and Blakeley, 1983) milk.

Indeed the EGF present in rat milk has been shown to be significant for the normal development of pups (Oka et al 1983). EGF has not, however, been found in bovine milk (Read 1985). Instead insulin-like growth factor (IGF) I and II (Francis et al, 1986) and bovine colostrum growth factor (BCGF), which is structurally related to Platelet-derived Growth Factor (PDGF) (Shing and Klagsbrun, 1984, Brown and Blakeley, 1984), have been identified.

EP0457565 discloses milk protein hydrolyzates and compositions which are effective in the conditioning of hair and skin.

The applicant has surprisingly discovered that bovine milk contains growth promoting activity for rat mammary fibroblast cell line (Rama 27), which is not significantly stimulated by IGF or PDGF.

Furthermore, they have identified peptide sequences which elicit this growth promoting activity.

The invention relates to a peptide or a salt thereof comprising an amino acid sequence substantially identical to the C-terminal end of the α-S2 casein precursor.

According to a first aspect of the present invention there is provided the use of a peptide or a salt thereof comprising an amino acid sequence of from 9–31 amino acids in length and which is substantially identical to the C-terminal end of an α-S2 casein precursor including homologues thereof in which:

i) one or more of the amino acids Leu, Ile and Val are replaced by one another;

ii) one or more of the amino acids Tyr and Phe are replaced by one another; and/or iii) one or more of the amino acids Arg and Lys are replaced by one another, for the manufacture of a medicament or foodstuff for promoting growth.

Whilst whole casein protein shows no growth activity, the applicant has identified a number of peptides, derived from the C-terminal end of Bovine α-S2 casein, which elicit growth promoting activity.

Indeed, the applicant has shown this growth promoting activity to be present in at least peptides of 9 to 31 amino acids in length which have been derived from the C-terminal end of Bovine α-S2 casein. It is reasonable to hypothesise that the natural sequence responsible for the growth promoting activity is the sequence comprising the last 9 amino acids of the C-terminal end or an even shorter sequence from within the 9 amino acid sequence, possibly an 8 or 7 amino acid sequence. Indeed, it may be as short as a 3 amino acid sequence.

The bovine α-S2 casein precursor is characterised in that it has an amino acid sequence:

[CAS2_BOVIN] ALPHA-S2 CASEIN PRECURSOR.
SEQUENCE

MKFFIFTCLL AVALAKNTME HVSSSEESII SQETYKQEKN MAINPSKENL CSTFCKEVVR   (SEQ ID NO:6)

NANEEEYSIG SSSEESAEVA TEEVKITVDD KHYQKALNEI NQFYQKFPQY LQYLYQGPIV

LNPWDQVKRN AVPITPTLNR EQLSTSEENS KKTVDMESTE VFTKKTKLTE EEKNRLNFLK

KISQRYQKFA LPQYLKTVYQ HQKAMKPWIQ PKTKVIPYVR YL

In three letter codes this translates to:

[CAS2 BOVIN] ALPHA-S2 CASE IN PRECURSOR.
SEQUENCE

MetLysPhePheIlePheThrCysLeuLeu   (SEQ ID NO:6)
AlaValAlaLeuAlaLysAsnThrMetGlu

HisValSerSerSerGluGluSerIleIle
SerGlnGluThrTyrLysGlnGluLysAsn

MetAlaIleAsnProSerLysGluAsnLeu
CysSerThrPheCysLysGluValValArg

AsnAlaAsnGluGluGluTyrSerIleGly
SerSerSerGluGluSerAlaGluValAla

ThrGluGluValLysIleThrValAspAsp
LysHisTyrGlnLysAlaLeuAsnGluIle

AsnGlnPheTyrGlnLysPheProGlnTyr
LeuGlnTyrLeuTyrGlnGlyProIleVal

LeuAsnProTrpAspGlnValLysArgAsn
AlaValProIleThrProThrLeuAsnArg

GluGlnLeuSerThrSerGluGluAsnSer
LysLysThrValAspMetGluSerThrGlu

ValPheThrLysLysThrLysLeuThrGlu
GluGluLysAsnArgLeuAsnPheLeuLys

LysIleSerGlnArgTyrGlnLysPheAla
LeuProGlnTyrLeuLysThrValTyrGln

HisGlnLysAlaMetLysProTrpIleGln
ProLysThrLysValIleProTyrValArg

TyrLeu

The applicant has found that short peptide sequences incorporating the C-terminal sequence -LysValIleProTyrValArgTyrLeu (SEQ ID NO:1) show growth promoting activity.

According to a second aspect of the present invention there is provided a growth factor comprising the amino acid sequence -LysValIleProTyrValArgTyrLeu (SEQ ID NO:1).

Furthermore, comparison of, for example, the last 20 amino acids of the C-terminal sequence for bovine α-S2 casein with those for goat, and sheep shows a high degree of homology as does to a lesser extent the C-terminal amino acid sequence of rabbit and pig α-S2 casein.

The sequences for these are set out below.

[CAS2_CAPHI] ALPHA-S2 CASEIN PRECURSOR (ALPHA-S2-CN).
SEQUENCE

MKFFIFTCLL AVALAKHKME HVSSSEEPIN IFQEIYKQEK NMAIHPRKEK LCTTSCEEVV    (SEQ ID NO:7)

RNANEEEYSI RSSSEESAEV APEEIKITVD DKHYQKALNE INQFYQKFPQ YLQYPYQGPI

VLNPWDQVKR NAGPFTPTVN REQLSTSEEN SKKTIDMEST EVFTKKTKLT EEEKNRLNFL

KKISQYYQKF AWPQYLKTVD QHQKAMKPWT QPKTNAIPYV RYL

>pir|S33881|S33881 alphas2-casein E-goat

MKFFIFTCLL AVALAKHKME HVSSSEEPIN IFQEIYKQEK NMAIHPRKEK LCTTSCEEVV    (SEQ ID NO:8)

RNANEEEYSI RSSSEESAKV APEEIKITVD DKHYQKALNE INQFYQKFPQ YLQYPYQGPI

VLNPWDQVKR NAGPFTPTVN REQLSTSEEN SKKTIDMEST EVFTKKTKLT EEEKNRLNFL

KKISQYYQKF AWPQYLKTVD QHQKAMKPWT QPKTNAIPYV RYL 223

>gp|S74171|S74171_1 alpha s2-casein C [Capra hircus]

MKFFIFTCLL AVALAKHKME HVSSSEEPIN IFQEIYKQEK NMAIHPRKEK LCTTSCEEVV    (SEQ ID NO:9)

RNANEEEYSI RSSSEESA_E_V APEEIKITVD DKHYQKALNE INQFYQKFPQ YLQYPYQGPI

VLNPWDQVKR NAGPFTPTVN REQLSTSEEN SKKTIDMEST EVFTKKTKLT EEEKNRLNFL

K_I_ISQYYQKF AWPQYLKTVD QHQKAMKPWT QPKTNAIPYV RYL 223

>pir|S39776|S9776 alpha-S2-casein form b precursor-rabbit
>gp|X76909|OCPAS2BCS_1 pre-alpha S2b casein (AA -15 to 167)
[Oryctolagus cuniculus]

MKFFIFTCLL AVALAKPKIE QSSSEETIAV SQEVSPNLEN ICSTACEEPI KNINEVEYVE    (SEQ ID NO:10)

VPTEIKDQEF YQKVNLLQYL QALYQYPTVM DPWTRAETKA IPFIRTMQYK QEKDATKHTS

QKTELTEEEK AFLKYLDEMK QYYQKFVFPQ YLKNAHHFQK TMNPWNHVKT IIYQSVPTL 179

[CAS2_SHEEP] ALPHA-S2 CASEIN PRECURSOR.
SEQUENCE

MKFFIFTCLL AVALAKHKME HVSSSEEPIN ISQEIYKQEK NMAIHPRKEK LCTTSCEEVV    (SEQ ID NO:11)

RNADEEEYSI RSSSEESAEV APEEVKITVD DKHYQKALNE INQFYQKFPQ YLQYLYQGPI

VLNPWDQVKR NAGPFTPTVN REQLSTSEEN SKKTIDMEST EVFTKKTKLT EEEKNRLNFL

KKISQYYQKF AWPQYLKTVD QHQKAMKPWT QPKTNAIPYV RYL

[CAS2_PIG] ALPHA-S2 CASEIN PRECURSOR.
SEQUENCE

MKFFIFTCLL AVAFAKHEME HVSSSEESIN ISQEKYKQEK NVINHPSKED ICATSCEEAV    (SEQ ID NO:12)

RNIKEVGYAS SSSSEESVDI PAENVKVTVE DKHYLKQLEK ISQFYQKFPQ YLQALYQAQI

VMNPWDQTKT SAYPFIPTVI QSGEELSTSE EPVSSSQEEN TKTVDMESME EFTKKTELTE

EEKNRIKFLN KIKQYYQKFT WPQYIKTVHQ KQKAMKPWNH IKTNSYQIIP NLRYF

In three letter code these translate to:

[CAS2 CAPH1] ALPHA-S2 CASEIN PRECURSOR
(ALPHA-S2-CN).
SEQUENCE

MetLysPhePheIlePheThrCysLeuLeu    (SEQ ID NO:7)
AlaValAlaLeuAlaLysHisLysMetGlu

HisValSerSerSerGluGluProIleAsn
IlePheGlnGluIleTyrLysGlnGluLys

AsnMetAlaIleHisProArgLysGluLys
LeuCysThrThrSerCysGluGluValVal

ArgAsnAlaAsnGluGluGluTyrSerIle
ArgSerSerSerGluGluSerAlaGluVal

AlaProGluGluIleLysIleThrValAsp
AspLysHisTyrGlnLysAlaLeuAsnGlu

IleAsnGlnPheTyrGlnLysPheProGln

-continued
TyrLeuGlnTyrProTyrGlnGlyProIle

ValLeuAsnProTrpAspGlnValLysArg

AsnAlaGlyProPheThrProThrValAsn

ArgGluGlnLeuSerThrSerGluGluAsn

SerLysLysThrIleAspMetGluSerThr

GluValPheThrLysLysThrLysLeuThr

GluGluGluLysAsnArgLeuAsnPheLeu

LysLysIleSerGlnTyrTyrGlnLysPhe

AlaTrpProGlnTyrLeuLysThrValAsp

GlnHisGlnLysAlaMetLysProTrpThr

GlnProLysThrAsnAlaIleProTyrVal

ArgTyrLeu

>pir/S33881/S33881 alpha S2-casein E goat

MetLysPhePheIlePheThrCysLeuLeu        (SEQ ID NO:8)

AlaValAlaLeuAlaLysHisLysMetGlu

HisValSerSerSerGluGluProIleAsn

IlePheGlnGluIleTyrLysGlnGluLys

AsnMetAlaIleHisProArgLysGluLys

LeuCysThrThrSerCysGluGluValVal

ArgAsnAlaAsnGluGluGluTyrSerIle

ArgSerSerSerGluGluSerAlaLysVal

AlaProGluGluIleLysIleThrValAsp

AspLysHisTyrGlnLysAlaLeuAsnGlu

IleAsnGlnPheTyrGlnLysPheProGln

TyrLeuGlnTyrProTyrGlnGlyProIle

ValLeuAsnProTrpAspGlnValLysArg

AsnAlaGlyProPheThrProThrValAsn

ArgGluGlnLeuSerThrSerGluGluAsn

SerLysLysThrIleAspMetGluSerThr

GluValPheThrLysLysThrLysLeuThr

GluGluGluLysAsnArgLeuAsnPheLeu

LysLysIleSerGlnTyrTyrGlnLysPhe

AlaTrpProGlnTyrLeuLysThrValAsp

GlnHisGlnLysAlaMetLysProTrpThr

GlnProLysThrAsnAlaIleProTyrVal

ArgTyrLeu 223

>pir/S74171/S74171 1 alpha S2-casein C
[Capra hircus]

MetLysPhePheIlePheThrCysLeuLeu        (SEQ ID NO:9)

AlaValAlaLeuAlaLysHisLysMetGlu

HisValSerSerSerGluGluProIleAsn

IlePheGlnGluIleTyrLysGlnGluLys

AsnMetAlaIleHisProArgLysGluLys

-continued
LeuCysThrThrSerCysGluGluValVal

ArgAsnAlaAsnGluGluGluTyrSerIle

ArgSerSerSerGluGluSerAlaGluVal

AlaProGluGluIleLysIleThrValAsp

AspLysHisTyrGlnLysAlaLeuAsnGlu

IleAsnGlnPheTyrGlnLysPheProGln

TyrLeuGlnTyrProTyrGlnGlyProIle

ValLeuAsnProTrpAspGlnValLysArg

AsnAlaGlyProPheThrProThrValAsn

ArgGluGlnLeuSerThrSerGluGluAsn

SerLysLysThrIleAspMetGluSerThr

GluValPheThrLysLysThrLysLeuThr

GluGluGluLysAsnArgLeuAsnPheLeu

LysIleIleSerGlnTyrTyrGlnLysPhe

AlaTrpProGlnTyrLeuLysThrValAsp

GlnHisGlnLysAlaMetLysProTrpThr

GlnProLysThrAsnAlaIleProTyrVal

ArgTyrLeu 223

>pir/S39776/S39776 alpha-S2-
Casein form b precursor-rabbit
>gp/X76909/OCPAS2BCS 1 pre-alpha S"b casein
(AA -15 to 167)
[Oryctolagus cuniculus]

MetLysPhePheIlePheThrCysLeuLeu        (SEQ ID NO:10)

AlaValAlaLeuAlaLysProLysIleGlu

GlnSerSerSerGluGluThrIleAlaVal

SerGlnGluValSerProAsnLeuGluAsn

IleCysSerThrAlaCysGluGluProIle

LysAsnIleAsnGluValGluTyrValGlu

ValProThrGluIleLysAspGlnGluPhe

TyrGlnLysValAsnLeuLeuGlnTyrLeu

GlnAlaLeuTyrGlnTyrProThrValMet

AspProTrpThrArgAlaGluThrLysAla

IleProPheIleArgThrMetGlnTyrLys

GlnGluLysAspAlaThrLysHisThrSer

GlnLysThrGluLeuThrGluGluGluLys

AlaPheLeuLysTyrLeuAspGluMetLys

GlnTyrTyrGlnLysPheValPheProGln

TyrLeuLysAsnAlaHisHisPheGlnLys

ThrMetAsnProTrpAsnHisValLysThr

IleIleTyrGlnSerValProThrLeu

179

-continued
[CAS2 SHEEP] ALPHA-S2 CASEIN PRECURSOR SEQUENCE.

MetLysPhePheIlePheThrCysLeuLeu (SEQ ID NO:11)

AlaValAlaLeuAlaLysHisLysMetGlu

HisValSerSerSerGluGluProIleAsn

IleSerGlnGluIleTyrLysGlnGluLys

AsnMetAlaIleHisProArgLysGluLys

LeuCysThrThrSerCysGluGluValVal

ArgAsnAlaAspGluGluGluTyrSerIle

ArgSerSerSerGluGluSerAlaGluVal

AlaProGluGluValLysIleThrValAsp

AspLysHisTyrGlnLysAlaLeuAsnGlu

IleAsnGlnPheTyrGlnLysPheProGln

TyrLeuGlnTyrLeuTyrGlnGlyProIle

ValLeuAsnProTrpAspGlnValLysArg

AsnAlaGlyProPheThrProThrValAsn

ArgGluGlnLeuSerThrSerGluGluAsn

SerLysLysThrIleAspMetGluSerThr

GluValPheThrLysLysThrLysLeuThr

GluGluGluLysAsnArgLeuAsnPheLeu

LysLysIleSerGlnTyrTyrGlnLysPhe

AlaTrpProGlnTyrLeuLysThrValAsp

GlnHisGlnLysAlaMetLysProTrpThr

GlnProLysThrAsnAlaIleProTyrVal

ArgTyrLeu

[CAS2 PIG] ALPHA-S2 CASEIN PRECURSOR. SEQUENCE

MetLysPhePheIlePheThrCysLeuLeu (SEQ ID NO:12)

AlaValAlaPheAlaLysHisGluMetGlu

HisValSerSerSerGluGluSerIleAsn

IleSerGlnGluLysTyrLysGlnGluLys

AsnValIleAsnHisProSerLysGluAsp

IleCysAlaThrSerCysGluGluAlaVal

ArgAsnIleLysGluValGlyTyrAlaSer

SerSerSerSerGluGluSerValAspIle

ProAlaGluAsnValLysValThrValGlu

AspLysHisTyrLeuLysGlnLeuGluLys

IleSerGlnPheTyrGlnLysPheProGln

TyrLeuGlnAlaLeuTyrGlnAlaGlnIle

ValMetAsnProTrpAspGlnThrLysThr

SerAlaTyrProPheIleProThrValIle

-continued
GlnSerGlyGluGluLeuSerThrSerGlu

GluProValSerSerSerGlnGluGluAsn

ThrLysThrValAspMetGluSerMetGlu

GluPheThrLysLysThrGluLeuThrGlu

GluGluLysAsnArgIleLysPheLeuAsn

LysIleLysGlnTyrTyrGlnLysPheThr

TrpProGlnTyrIleLysThrValHisGln

LysGlnLysAlaMetLysProTrpAsnHis

IleLysThrAsnSerTyrGlnIleIlePro

AsnLeuArgTyrPhe

It will be apparent from this that the C-terminal sequence can vary from species to species and that consequently whilst the preferred sequences comprise those derived from the C-terminal end of the bovine α-S2 casein those of the other species might be used.

Furthermore, due to the similar nature of some amino acids it is possible that minor substitutions may have little effect on the functioning of the sequence.

Thus, for example, Leucine, isoleucine and valine may be interchanged. Tyrosine and phenylalanine may be interchanged, and arginine and lysine may be interchanged.

The significance of the discovery is that a peptide supplement which can promote growth can be added to food or drink products, for both human or animal consumption.

According to a further aspect of the present invention there is provided a food or drink product comprising a peptide or salt thereof of the invention.

Preferably the food or drink product is an infant formula or an animal feed. It may be in liquid or powder form.

Whilst it is possible to synthetically produce peptides according to the present invention it would be desirable to produce the peptide in situ from cows milk.

According to a further aspect of the present invention milk is treated with an enzyme to break the casein in the milk into smaller fragments containing the active peptide or a salt thereof of the invention.

Preferably the enzyme is a protease and more particularly one which cleaves lysine cross-bonds. More preferably still it is plasmin or trypsin.

The invention will be further described by way of example only with reference to the following examples:

EXAMPLE 1

The growth promoting activity of different milk types was determined by precipitating caseins and assaying the supernatants for their ability to stimulate the incorporation of [3H] thymidine into the DNA of Rama 27 cells by known methodology (Smith et al, 1984).

Figure 1:
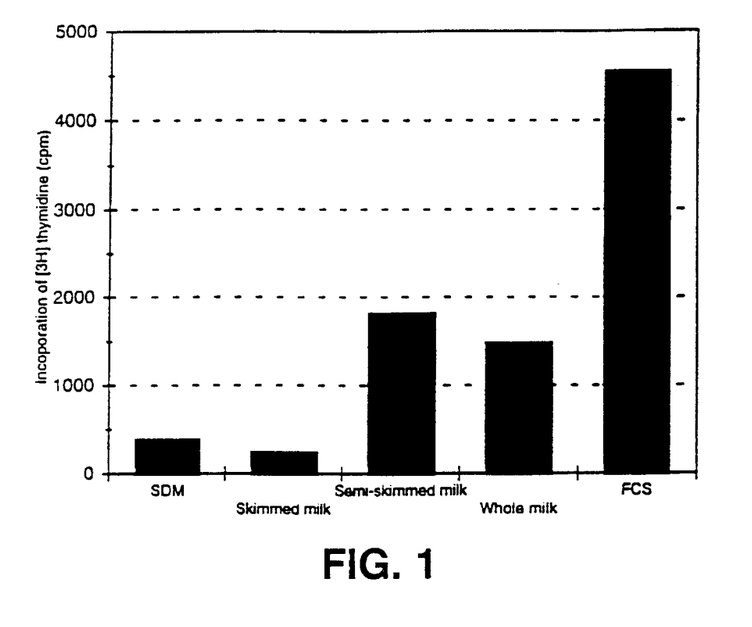

The results of the tests are illustrated in FIG. 1, which shows the growth-promoting activity of different milk types. Three sorts of commercial milks were acidified to precipitate the caseins and assayed for their growth promoting activity. The greatest activity was found in semi-skimmed milk. SDM (step down medium) represents the negative control and FCS (foetal calf serum) represents the positive control.

EXAMPLE 2

5 liters of semi-skimmed milk was made to pH 3.0 with HCl and left for 2 hours at 4° C. It was centrifuged in a Sorvall RC5B centrifuge at 9000 rpm in a GS3 rotor for 40 min, and the supernatant (approximately 3.6 liters) was poured through glass wool to remove fat. Solid $(NH_4)_2SO_4$ was added slowly to the supernatant with stirring at 4° C. to a concentration of 22% (w/v), and was left for 2 hours at 4° C. without stirring. Precipitated protein was removed by centrifugation as above. To the supernatant was added further $(NH_4)_2SO_4$ to a concentration of 35% (w/v) and the precipitate recovered as above. The precipitate was redissolved in 1600 ml distilled water and dialyzed against running tap water overnight, then against 20 mM $NaH_2PO_4$, pH 6.0, for 8 hours.

Figure 2:
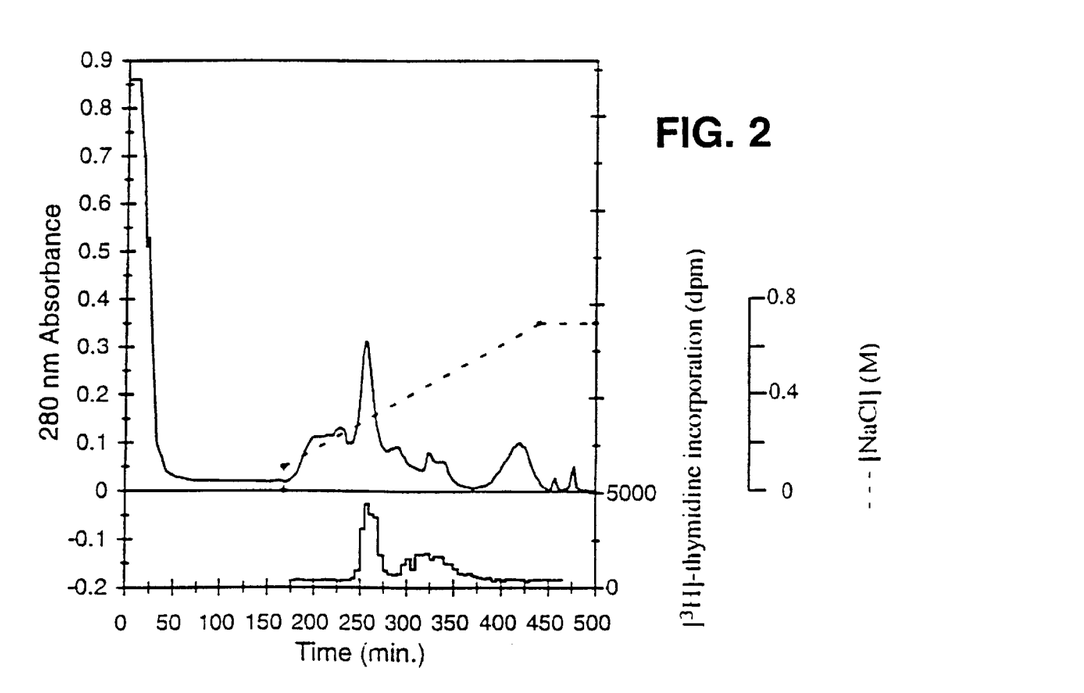

The active fractions were obtained using a series of chromatographic techniques as outlined in (i) to (iv) below:

(i) The active fraction prepared as above was subjected to CM-Sepharose chromatography. It was added to a column of CM-Sepharose (10 cm×5 cm id, Pharmacia) that had been pre-equilibrated with 20 mM Sodium phosphate buffer pH 6.0. After loading, the column was washed with 500 ml of 50 mM NaCl in the same buffer. Protein was eluted with a 1500 ml linear gradient of 0.1 to 0.7M NaCl in 20 mM sodium phosphate buffer pH 6.0. The bioactive fractions eluted at 0.28M NaCl and approximately 0.4M NaCl—see FIG. 2. In FIG. 2 the upper panel shows the absorbance of the protein at 280 nm and the lower panel shows the activity (The incorporation of $^3$H-thymidine into DNA). The sample was from material precipitating between 22 to 35% $(NH_4)_2SO_4$. After being redissolved and dialyzed it was loaded into the column (10 cm×5 cm) with 0.05 M NaCl in 20 mM $NaH_2PO_4$, pH 6.0. The eluting gradient was 0.1–0.7 M NaCl in 20 mM $NaH_2PO_4$, pH 6. The flowrate was 5 ml/min, the fraction size was 25 ml each. Two activities eluted at 0.28 M NaCl and 0.34–0.45 M NaCl respectively. The high absorbance at 280 nm at the beginning of the trace indicates the amount of unbound protein. The fraction-eluted at 0.28 M NaCl was used for further purification.

Figure 3:
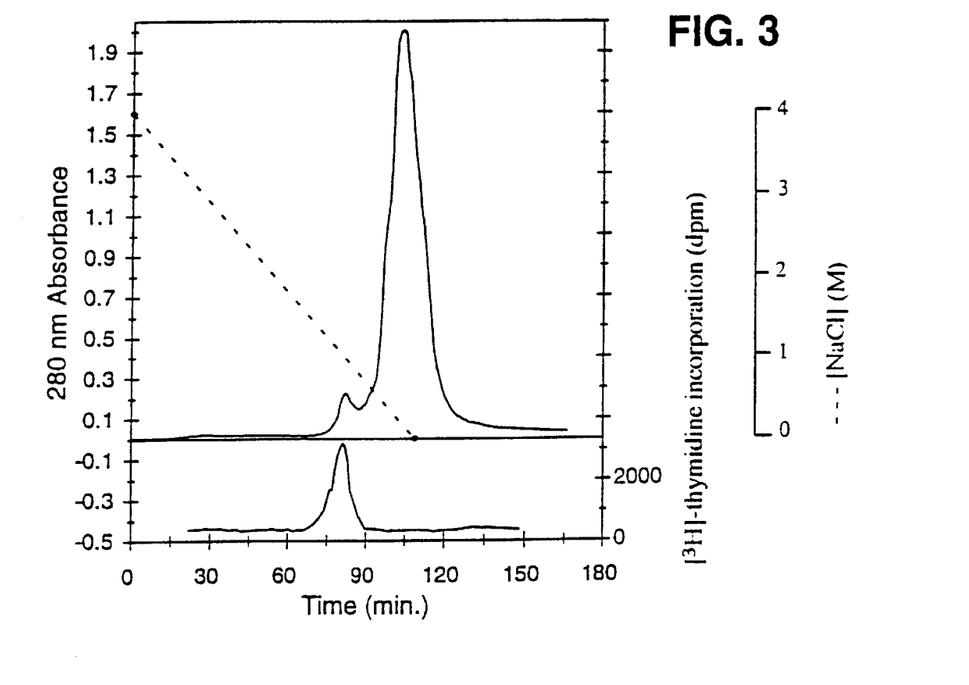

(ii) The active fractions from the above separation were subjected to hydrophobic interaction chromatography. It was made 3.7M with NaCl in 20 mM $NaH_2PO_4$, pH 6.5, and applied to a butyl Sepharose column (8.6 cm×2.5 cm id) that had been pre-equilibrated with 4M NaCl in 20 mM $NaH_2PO_4$, pH 6.5. Protein was eluted with a decreasing gradient of NaCl as indicated in FIG. 3. In FIG. 3 the upper panel shows the absorbance of the protein at 280 nm and the lower panel shows the activity (The incorporation of $^3$H-thymidine into DNA). The sample was from the early activity after CM-Sepharose chromatography. The column (2.5 cm×8.6 cm, butyl bonded Sepharose) had been equilibrated with 4 M NaCl in 20 mM $NaH_2PO_4$, pH 6.5. The flowrate was 3.5 ml/min and fraction size was 3.5 ml. The activity eluted at 1.6 M NaCl, just before the major protein peak.

Figure 4:
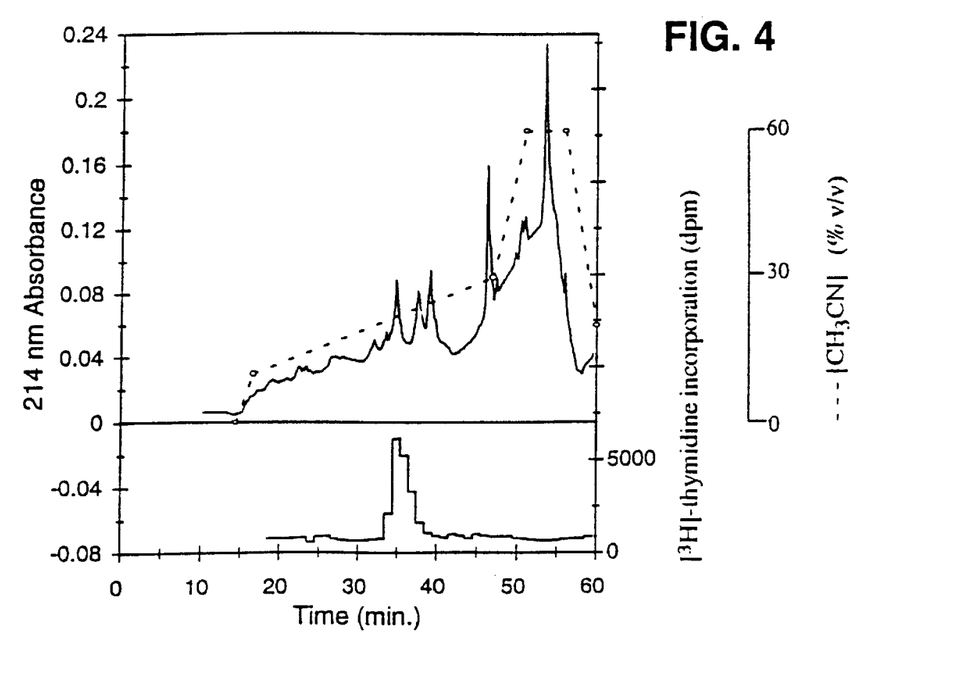

(iii) The active fractions from the hydrophobic interaction column were subjected to Reversed Phased HPLC-1 chromatography. It was applied in 8 batches to a butyl reversed phase column (Brownlee, 300 A pore size, 7 μm particle size, 25 cm×4.6 mm id) that had been pre-equilibrated with 0.1% TFA. After washing the column with 0.1% TFA, protein was eluted with a gradient of acetonitrile (far uv grade, Rathburns, Walkerburn, Scotland) as indicated in FIG. 4. In FIG. 4 the upper panel shows the absorbance of the protein at 214 nm and the lower panel shows the activity (The incorporation of $^3$H-thymidine into DNA). The sample was from the activity after hydrophobic interaction chromatography. The column (250 cm×4.6 mm, C4) had been equilibrated with 0.1% TFA. The flow rate was 0.7 ml/min and fraction size was 0.7 ml. The eluting gradient was 10 to 30% acetonitrile in 0.1%. TFA in 30 min. The activity eluted at 23% acetonitrile.

Figure 5:
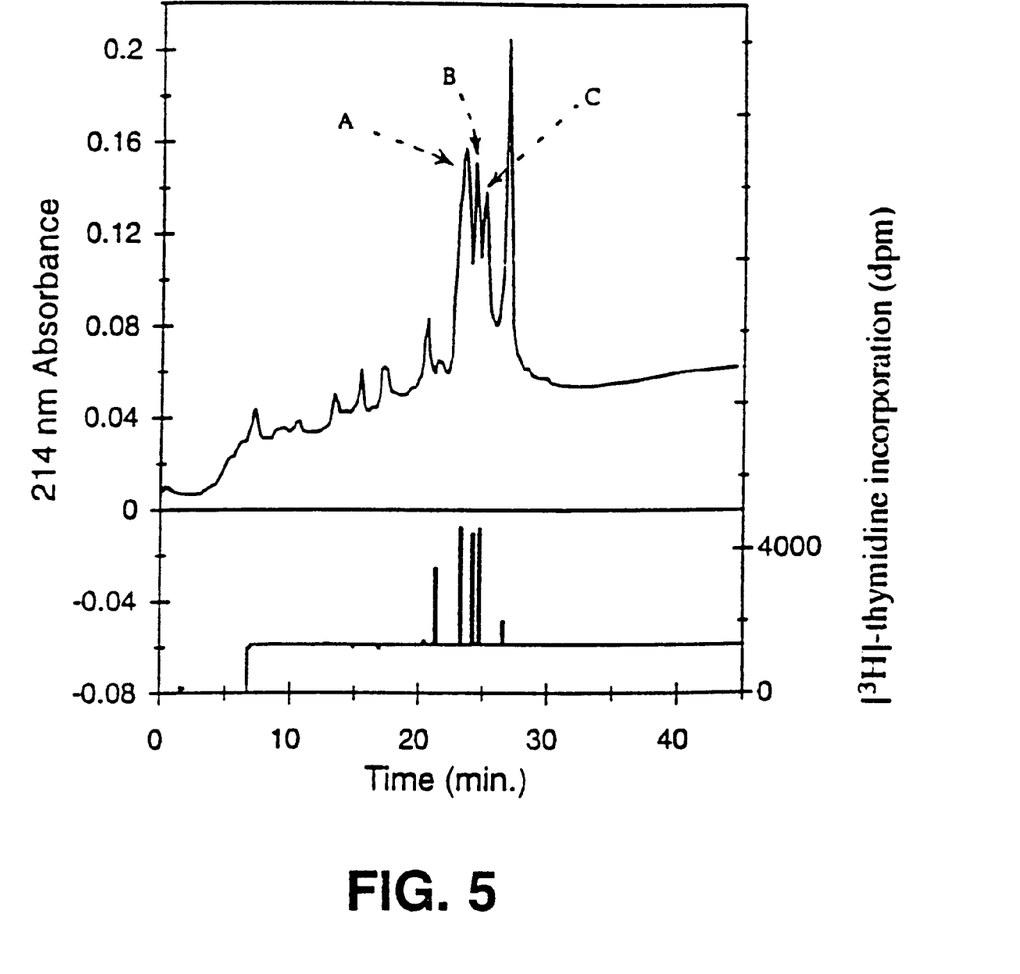
Figure 6:
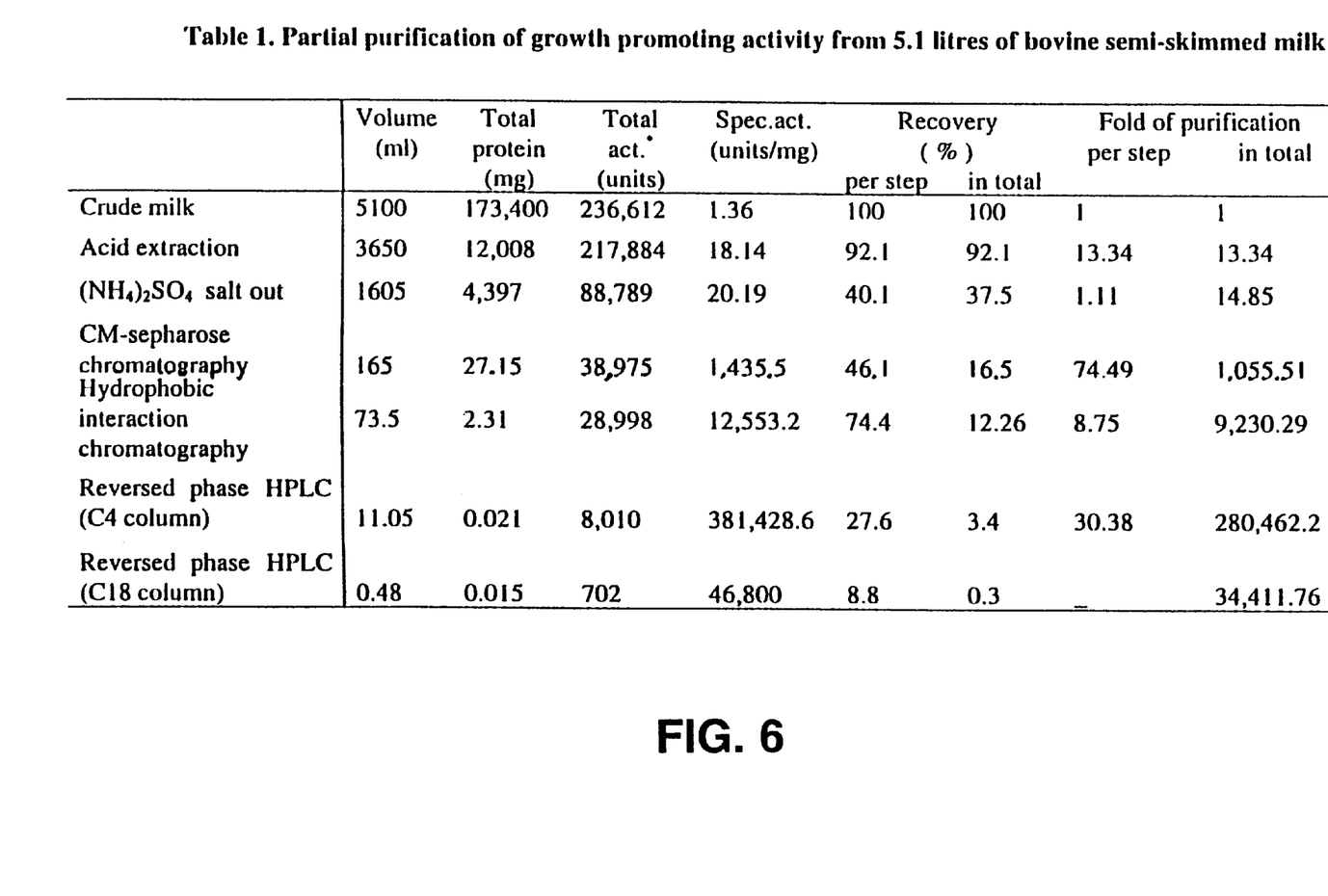

(iv) The active fractions were then subjected to reversed phase HPLC-2 chromatography. The mitogenic fractions from all 8 batches of the above reversed phase chromatograms were pooled and concentrated on a centrifugal drier to a total volume of 100 μl. This concentrated material was loaded onto a C18 reversed phase column (ODS ultrasphere, Beckman) which had been pre-equilibrated with 0.1% TFA, and was eluted with a shallow gradient of 20 to 40% acetonitrile, 0.1% TFA over 45 min, at a flow rate of 0.2 ml/min. Absorbance was monitored at 214 nm, and material from each peak of absorbance was collected separately by hand—see FIG. 5. In FIG. 5 the upper panel shows the absorbance of the protein at 214 nm and the lower panel shows the activity (The incorporation of $^3$H-thymidine into DNA). The sample was from the activity after reversed phase HPLC-1. The column (ODS) had been equilibrated with 0.1% TFA. The flowrate was 0.2 ml/min. Each absorption peak at 214 nm was collected manually. The eluting gradient was 20 to 40% acetonitrile in 0.1% TFA in 45 min. The peaks A,B,C (arrows) were all active.

The purified proteins (peaks A,B,C) obtained in step (iv) were then analysed.

Protein content was measured by the binding of Coomassie Blue according to the Bio-Rad protocol, using bovine gamma globulin as standard. Peptide quantification of fractions separated by HPLC was by their absorbance at 214 nm, using cytochrome c and lysozyme as standards.

The protein fractions A,B,C, of the casein digest where assayed for their ability to stimulate the incorporation of [3H] thymidine into the DNA of Rama 27 cells exactly as described previously.

The results are illustrated in Table 1 which shows the growth promoting activity of progressively purified fractions of Ó-S2 casein. In table 1, * indicates one unit of activity is defined as the amount of protein required to produce half maximal stimulation compared with 1% FCS when added to R27 cells.

The peptides from the peaks B and C of reversed phase HPLC-2 were then sequenced. They were found to be a nested series of sequences of 5 peptides. They corresponded to the C-terminus of bovine Ó-S2 casein. The peak C was solely ThrLysValIleProTyrValArgTyrLeu (SEQ ID NO:2), the other sequences were from peak B.

The sequences of the peaks are identified below:

SEQ ID NO:1 LysValIleProTyrValArgTyrLeu

SEQ ID NO:2 ThrLysValIleProTyrValArgTyrLeu

SEQ ID NO:3 LysThrLysValIleProTyrValArgTyrLeu

AlaMetLysProTrpIleGln-
ProLysThrLysValIleProTyrValArgTyrLeu (peak B)

SEQ ID NO:5 ProGlnTyrLeuLysThrValTyrGln-
HisGlnLysAlaMetLysProTrpI-
leGlnProLysThrLysValIleProTyrValArgTyrLeu (peak B)

To ascertain that the activity was not due to impurities identical peptide sequences were synthesized on a Milligen/Biosearch 9050 peptide synthesizer (Millipore, Watford) using Fmoc chemistry and pentafluorophenyl esters according to the standard protocol.

Of these initially only LysValIleProTyrValArgTyrLeu (SEQ ID NO:1) showed bioactivity, but after storage in PBS all the peptides acquired a low level of mitogenicity. The activity of LysValIleProTyrValArgTyrLeu (SEQ ID NO:1) was substantially increased when maintained at alkaline pH. By way of contrast alpha-casein was inactive in the mitogenic assay. On digestion with trypsin, activity in the assay was generated, which was separable by reversed phase HPLC from that due to trypsin itself.

The example described herein demonstrates that the growth factor activity of milk is largely due to C-terminal fragments of α-S2 casein.

Given the activity of the peptide it is expected that the addition of from 0.1 µg to 10 µg, more particularly about 1 µg of peptide to 250 g of feed or drink will provide good growth promotion activity.

However, in order to maintain the activity the synthetic peptides should be stored in alkaline conditions, preferably at about pH 13.

What is claimed is:

1. A food or drink product comprising a peptide or a salt thereof comprising an amino acid sequence of from 9–31 amino acids in length and which is substantially identical to the C-terminal end of an α-S2 casein precursor or a homologue thereof in which
   i) one or more of the amino acids Leu, Ile and Val are replaced by one another;
   ii) one or more of the amino acids Tyr and Phe are replaced by one another; and/or
   iii) one or more of the amino acids Arg and Lys are replaced by one another.

2. A method of producing a medicament or foodstuff comprising a growth promoting peptide comprises treating milk with an enzyme to break milk casein present in the milk into one or more peptides comprising an amino acid sequence of from 9–31 amino acids in length and which is substantially identical to the C-terminal end of the α-S2 casein precursor.

3. The product of claim 1 wherein the peptide is derived from bovine, goat, sheep, rabbit or pig α-S2 casein or is a synthesized equivalent or a homologue thereof.

4. The product of claim 3 wherein the peptide is derived from bovine α-S2 casein or is a synthesized equivalent or a homologue thereof.

5. The product of claim 4 wherein the peptide comprises 9 amino acids.

6. A peptide consisting of the amino acid sequence: Lys Val Ile Pro Tyr Val Arg Tyr Leu (SEQ ID No: 1).

7. A peptide consisting of the amino acid sequence: Thr Lys Val Ile Pro Tyr Val Arg Tyr Leu (SEQ ID No: 2).

8. A peptide consisting of the amino acid sequence: Lys Thr Lys Val Ile Pro Tyr Val Arg Tyr Leu (SEQ ID No: 3).

9. A peptide consisting of the amino acid sequence: Ala Met Lys Pro Trp Ile Gln Pro Lys Thr Lys Val Ile Pro Tyr Val Arg Tyr Leu (SEQ ID No: 4).

10. A peptide consisting of the amino acid sequence: Pro Gln Tyr Leu Lys Thr Val Tyr Gln His Gln Lys Ala Met Lys Pro Trp Ile Gln Pro Lys Thr Lys Val Ile Pro Tyr Val Arg Tyr Leu (SEQ ID No: 5).

11. The product of claim 1 which is an infant formula or an animal feed.

12. The product of claim 1 which is a liquid or powder.

13. The product of claim 1 which comprises whole milk or semi-skimmed milk.

14. The product of claim 1 which has an alkaline pH.

15. The product of claim 1 in which the peptide is present in amount of from about 0.1 to about 10 µg in about 250 g of product.

16. The method of claim 2 wherein the peptide is derived from bovine, goat, sheep, rabbit or pig α-S2 casein or is a synthesized equivalent or a homologue thereof.

17. The method of claim 16 wherein the peptide is derived from bovine α-S2 casein or is a synthesized equivalent or a homologue thereof.

18. The method of claim 17 wherein the peptide comprises 9 amino acids.

19. The method of claim 18 wherein the peptide comprises the amino acid sequence: Lys Val Ile Pro Tyr Val Arg Tyr Leu (SEQ ID No: 1).

20. The method of claim 17 wherein the peptide comprises the amino acid sequence: Thr Lys Val Ile Pro Tyr Val Arg Tyr Leu (SEQ ID No: 2).

21. The method of claim 17 wherein the peptide comprises the amino acid sequence: Lys Thr Lys Val Ile Pro Tyr Val Arg Tyr Leu (SEQ ID No: 3).

22. The method of claim 17 wherein the peptide comprises the amino acid sequence: Ala Met Lys Pro Trp Ile Gln Pro Lys Thr Lys Val Ile Pro Tyr Val Arg Tyr Leu (SEQ ID No: 4).

23. The method of claim 17 wherein the peptide is the amino acid sequence: Pro Gln Tyr Leu Lys Thr Val Tyr Gln His Gln Lys Ala Met Lys Pro Trp Ile Gln Pro Lys Thr Lys Val Ile Pro Tyr Val Arg Tyr Leu (SEQ ID No: 5).

24. The method of claim 2 in which the medicament or foodstuff is an infant formula or an animal feed.

25. The method of claim 2 in which the medicament or foodstuff is a liquid or powder.

26. The method of claim 2 in which the medicament or foodstuff comprises whole milk or semi-skimmed milk.

27. The method of claim 2 in which the medicament or foodstuff has an alkaline pH.

28. The method of claim 2 in which the peptide is present in amount of from about 0.1 to about 10 µg in about 250 g of product.

* * * * *